(12) United States Patent
Nugara et al.

(10) Patent No.: US 8,840,920 B2
(45) Date of Patent: Sep. 23, 2014

(54) COMPOSITE STRUCTURE INCLUDING A LOW VINYL ACETATE LAYER

(75) Inventors: Peter N. Nugara, Richmond, VA (US); Bruce C. Begnoche, Midlothian, VA (US); Stephen K. Franzyshen, Richmond, VA (US); Fenghua Deng, Richmond, VA (US); Daniel C. Sanders, Richmond, VA (US); Christine A. Creegan, Richmond, VA (US); Steven R. Cosentino, Quinton, VA (US)

(73) Assignee: DuPont Teijin Films U.S. Limited Partnership, Chester, VA (US)

( * ) Notice: Subject to any disclaimer, the term of this patent is extended or adjusted under 35 U.S.C. 154(b) by 0 days.

(21) Appl. No.: 12/890,291

(22) Filed: Sep. 24, 2010

(65) Prior Publication Data

US 2011/0052789 A1 Mar. 3, 2011

Related U.S. Application Data

(60) Division of application No. 11/793,045, filed as application No. PCT/US2005/038759 on Oct. 26, 2005, now abandoned, which is a continuation of application No. 11/013,131, filed on Dec. 15, 2004, now abandoned.

(51) Int. Cl.
*A61K 9/70* (2006.01)
*B32B 27/08* (2006.01)

(52) U.S. Cl.
CPC .............. *A61K 9/703* (2013.01); *A61K 9/7084* (2013.01)
USPC ........................................................ 424/449

(58) Field of Classification Search
CPC ............................. A61K 9/7084; A61K 9/703
See application file for complete search history.

(56) References Cited

U.S. PATENT DOCUMENTS

| RE24,906 E | 12/1960 | Ulrich |
| 3,107,139 A | 10/1963 | Cormforth et al. |

(Continued)

FOREIGN PATENT DOCUMENTS

| EP | 0 641 647 A2 | 3/1995 |
| EP | 1 044 684 A2 | 10/2000 |

(Continued)

OTHER PUBLICATIONS

Shell Bitumen, Industrial Handbook (2005), p. 164.

(Continued)

*Primary Examiner* — Rachael E Bredefeld
(74) *Attorney, Agent, or Firm* — RatnerPrestia

(57) ABSTRACT

A composite structure suitable for making transdermal delivery devices includes in sequence: (a) a liner film layer; (b) a containment layer having from zero to 15 wt % content of vinyl acetate repeating units, the layer including either a thermal bonding copolyester resin or a combination of an ethylene-vinyl acetate component and a nonpolar polymer; and (c) a polyester film layer less than 20 µm in thickness. A drug layer lies either between the liner film layer and the containment layer or within a concave depression in the containment layer.

A composition including an ethylene-vinyl acetate component and an ABA block copolymer, wherein the A segments of the block copolymer are styrenic segments, is also provided. The composition includes between 1 and 15 wt % of vinyl acetate repeating units, based on the total weight of composition exclusive of any solvents.

16 Claims, 3 Drawing Sheets

(56) References Cited

U.S. PATENT DOCUMENTS

| | | | |
|---|---|---|---|
| 3,239,478 A | 3/1966 | Harlan, Jr. | |
| 3,871,947 A | 3/1975 | Brekken | |
| 3,935,338 A | 1/1976 | Robertson | |
| 4,165,210 A | 8/1979 | Corbett | |
| 4,181,752 A | 1/1980 | Martens et al. | |
| 4,379,454 A | 4/1983 | Campbell et al. | |
| 4,917,676 A | 4/1990 | Heiber et al. | |
| 4,952,650 A | 8/1990 | Young et al. | |
| 4,994,267 A * | 2/1991 | Sablotsky | 514/182 |
| 5,151,309 A | 9/1992 | Dollinger | |
| 5,169,727 A | 12/1992 | Boardman | |
| 5,300,291 A * | 4/1994 | Sablotsky et al. | 424/78.18 |
| 5,498,417 A * | 3/1996 | Lhila et al. | 424/448 |
| 5,597,865 A | 1/1997 | Jackson | |
| 5,637,646 A | 6/1997 | Ellis | |
| 5,753,768 A | 5/1998 | Ellis | |
| 5,861,170 A | 1/1999 | Kissel | |
| 5,986,011 A | 11/1999 | Ellis | |
| 5,997,897 A | 12/1999 | Horstmann et al. | |
| 6,007,835 A | 12/1999 | Bon-Lapillonne et al. | |
| 6,080,456 A | 6/2000 | Fonteyne | |
| 6,099,943 A | 8/2000 | Moeller et al. | |
| 6,114,021 A * | 9/2000 | Pankratz et al. | 428/214 |
| 6,222,115 B1 | 4/2001 | Nakanishi | |
| 6,245,959 B1 * | 6/2001 | Ohira et al. | 602/41 |
| 6,358,604 B1 | 3/2002 | Peiffer et al. | |
| 7,220,473 B2 * | 5/2007 | Beier et al. | 428/40.2 |
| 2002/0009486 A1 | 1/2002 | Godbey | |
| 2003/0072792 A1 * | 4/2003 | Flanigan et al. | 424/449 |
| 2003/0082227 A1 | 5/2003 | Sournac et al. | |

FOREIGN PATENT DOCUMENTS

| | | | |
|---|---|---|---|
| EP | 1 547 589 A1 | 6/2005 | |
| GB | 1115007 | 5/1968 | |
| JP | 2001-172446 A | 6/2001 | |
| JP | 2004-339353 A | 12/2004 | |
| WO | WO83/01623 * | 5/1983 | C08G 18/00 |
| WO | WO 90/07940 | 7/1990 | |
| WO | WO 98/00118 A | 1/1998 | |
| WO | WO 02/22109 * | 3/2002 | |
| WO | WO 02/22109 A | 3/2002 | |
| WO | WO 02/053360 A2 | 7/2002 | |
| WO | WO 03/030880 | 4/2003 | |
| WO | WO 2004/019930 A | 3/2004 | |

OTHER PUBLICATIONS

Notice to File a Response for Korean Patent Application No. 10-2007-7016086 dated Sep. 3, 2013; 4 pages, and English Translation, 4 pages.

Japanese Non-Final Office Action dated Nov. 19, 2013 (translation).

* cited by examiner

COMPOSITE STRUCTURE INCLUDING A LOW VINYL ACETATE LAYER

This application is a Division of U.S. patent application Ser. No. 11/793,045, filed Jun. 14, 2007 now abandoned, which is the National Stage filing of PCT Application No. PCT/US2005/038759, filed Oct. 26, 2005, which is a continuation of U.S. application Ser. No. 11/013,131, filed Dec. 15, 2004 now abandoned, the entire contents of which applications are incorporated herein by reference.

FIELD OF THE INVENTION

The invention relates to composite film structures. More particularly, it relates to film structures incorporating a film layer having a low vinyl acetate content.

BACKGROUND OF THE INVENTION

The skin is the largest and most accessible organ of the human body. The permeability of the skin, and its ability to deliver drugs to the blood stream, makes it an ideal drug delivery route. Transdermal Drug Delivery (TDD) systems capitalize on this potential by delivering drugs through the skin, making them easier to administer. Such delivery systems, also known as "patches" have in recent years become an increasingly important means of administering drugs. These systems offer advantages, such as avoidance of the gastrointestinal tract and "first-pass" through the liver, application close to the site of action, sustained and easily adjustable action, which are typically not achievable by other modes of administration.

In practice, a TDD containing the agent or agents to be administered is placed onto a tissue of a host. The agent, which is releasably stored in a repository of the device, then diffuses or is otherwise transported to the host. Such delivery can be used for topical, transdermal, transmucosal, or other transtissue delivery of the agent to therapeutically treat local or systemic medical conditions. Patch devices can be used for pharmacological treatments, cosmetic treatments, nutriceutical treatments, and/or the like. Such systems have found increasing use in dispensing, in a time-controlled manner, a variety of pharmaceutical ingredients for such purposes as hormone replacement therapy, pain management, angina pectoris, smoking cessation, birth control, and neurological disorders such as Parkinson's disease.

Typical transdermal systems comprise some kind of backing material that contains the drug, reservoir or layer containing the drug, and an adhesive to attach the TDD to the user. The backing material, commonly a polyester, is inert to the drug (or drug formulation) and adhesive and does not permit any of the drug formulation to migrate through it. However, many TDD's include a layer between the backing layer and the drug consisting of an ethylene-vinyl acetate (EVA) copolymer, which is sometimes used to provide adhesion between adjacent layers. However, one disadvantage to using such layers is that delivery of the drug to the user may be slower than would be the case if the EVA layer were not there, potentially resulting in the need for a larger patch size to deliver the desired dosage. Thus there is a need for alternative ways of providing the adhesive function of the EVA layer while minimizing unwanted drug interactions and slowing of drug release.

SUMMARY OF THE INVENTION

In one aspect, the invention provides a composite structure including in sequence:

(a) a liner film layer;
(b) a containment layer having from zero to 15 wt % content of vinyl acetate repeating units, the layer including either a thermal bonding copolyester resin or a combination of an ethylene-vinyl acetate component and a nonpolar polymer; and
(c) a polyester film layer less than 20 µm in thickness.

The composite structure further includes a drug layer either between the liner film layer and the containment layer, or within a concave depression in the containment layer, with the depression facing the liner film layer.

In another aspect, the invention provides a composition including an ethylene-vinyl acetate component and an ABA block copolymer wherein the A segments of the block copolymer are styrenic segments. The composition including between 1 and 15 wt % of vinyl acetate repeating units, based on the total weight of composition exclusive of any solvents.

In yet another aspect, the invention provides a method of making a composite structure, the method including in sequence:

(a) applying to a surface of a substrate a liquid mixture including a diluent, an ethylene-vinyl acetate component, and a nonpolar polymer; and
(b) removing the diluent to provide a coating containing between 1 and 15 wt % of vinyl acetate repeating units.

DETAILED DESCRIPTION OF THE INVENTION

The invention provides composite film structures suitable, inter alia, for use as Transdermal Drug Delivery (TDD) devices. In particular, the composite structures of the invention include a containment layer having between 0 and 15 wt % vinyl acetate repeating unit content in the polymer(s) constituting it, thereby minimizing interactions between the layer and a drug contained within the TDD. This structure may provide a more rapid transfer of the drug to the user, thereby improving performance. A considerable variety of TDD devices may be prepared according to the invention, utilizing this feature.

The invention will next be illustrated with reference to the Figures, wherein the same numbers indicate the same elements in all Figures. Such Figures are intended to be illustrative rather than limiting and are included herewith to facilitate the explanation of the present invention. The Figures are not to scale, and are not intended to serve as engineering drawings.

Figure 1:
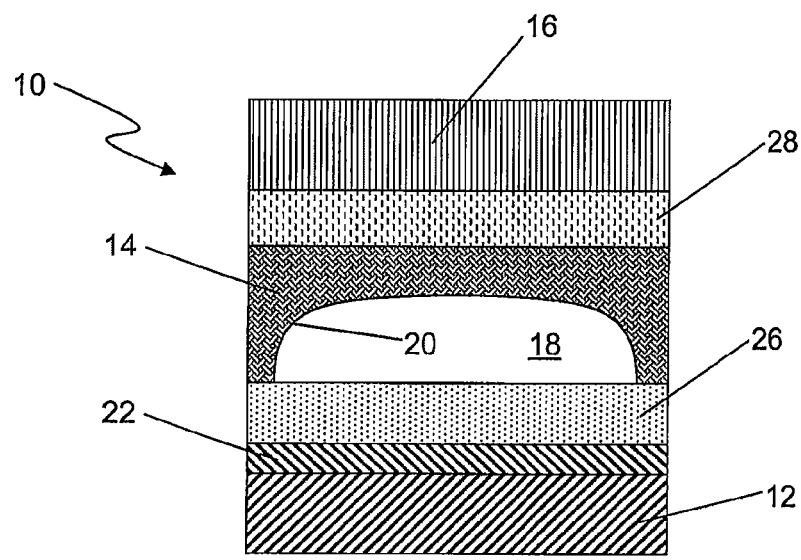
FIG. 1 is a sectional view of an exemplary composite structure according to one aspect of the invention, in which a drug layer is enclosed within a space defined by a membrane and a concave depression in a containment layer.

Referring now to FIG. 1, the invention provides a composite structure indicated generally at 10. The structure includes in sequence a liner film layer 12, an adhesive layer 22, an optional membrane 26, a containment layer 14 having a concave depression 20 containing a drug layer 18 that is in contact with the membrane 26, an optional primer layer 28, and a polyester film layer 16. The containment layer 14 is also in contact with the membrane 26.

Figure 2:
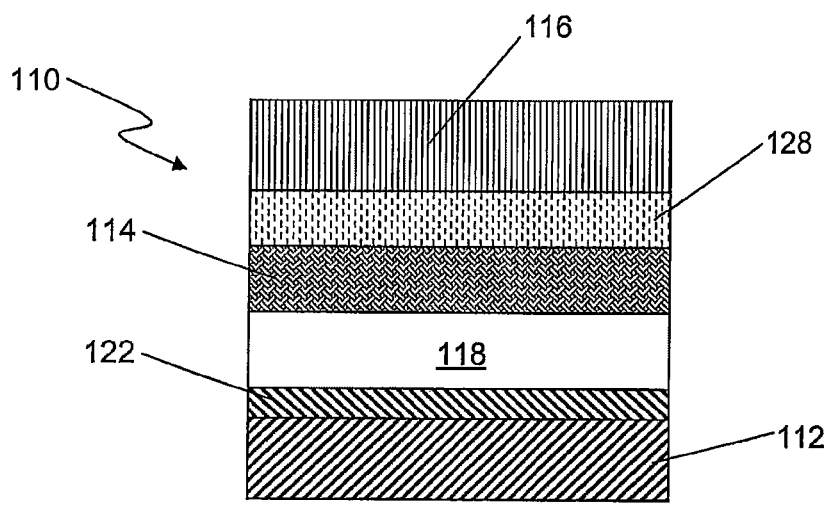
FIG. 2 is a sectional view of an exemplary composite structure according to another aspect of the invention, in which a drug layer is sandwiched between an adhesive layer and a containment layer.

FIG. 2 shows another composite structure, indicated generally at 110, according to the invention. The structure includes, in sequence, a liner film layer 112, an adhesive layer 122, a drug layer 118, a containment layer 114, an optional primer layer 128, and a polyester film layer 116.

Figure 3:
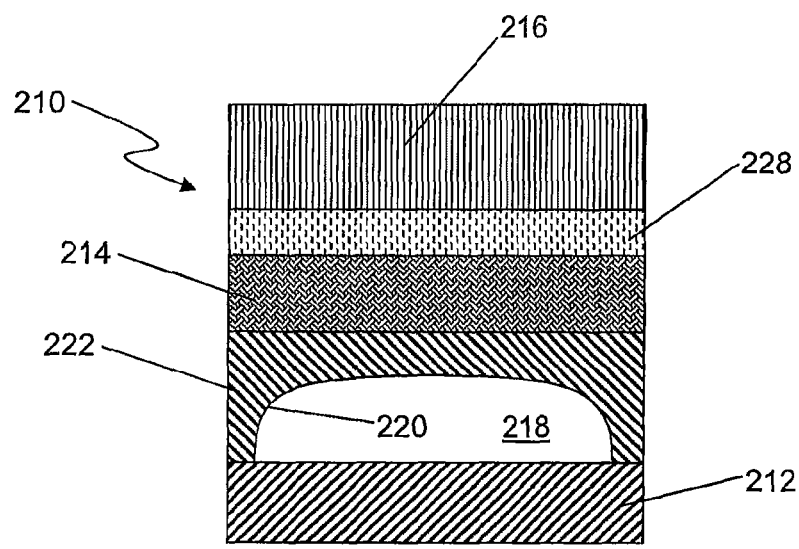
FIG. 3 is a sectional view of an exemplary composite structure according to a further aspect of the invention, in which a drug layer is enclosed within a space defined by a liner film layer and a concave depression in an adhesive layer.

Referring to FIG. 3, there is shown another composite structure, indicated generally at 210, according to the invention. The structure includes a liner film layer 212 and an adhesive layer 222 having a concave depression 220 containing a drug layer 218 that is in contact with the liner film layer 212. The adhesive is also in contact with the liner film layer 212, as well as with a containment layer 214. The containment layer 214 is connected to a polyester film layer 216 by way of an interposed (but optional) primer layer 228.

Figure 4:
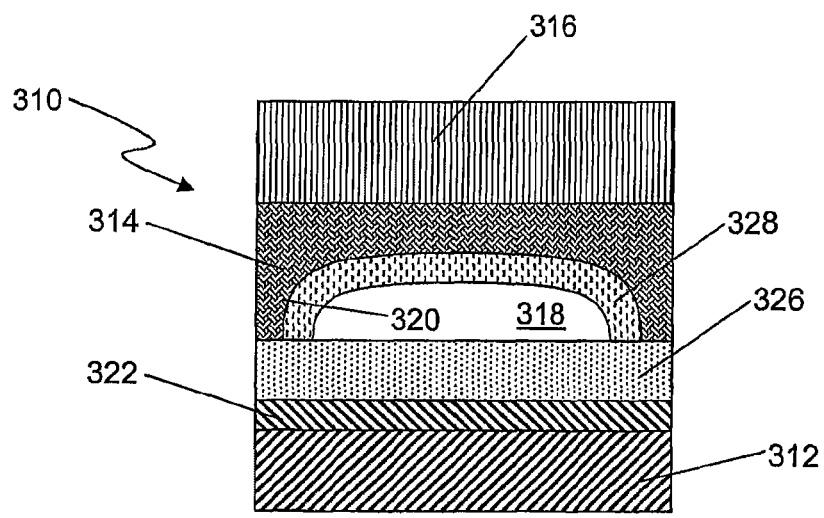
FIG. 4 is a sectional view of an exemplary composite structure according to still another aspect of the invention, in which a drug layer is enclosed within a space defined by a membrane and a primer-coated concave depression in a containment layer.

FIG. 4 shows another composite structure, indicated generally at 310, according to the invention. The structure includes, in sequence, a liner film layer 312, an adhesive layer 322, an optional membrane 326, and a drug layer 318 that is in contact with the membrane 326. The drug, which in this embodiment is in contact with an optional primer layer 328, is contained in a concave depression 320 within a containment layer 314. The containment layer 314 is in contact with the membrane 326 and with a polyester film layer 316.

Figure 5:
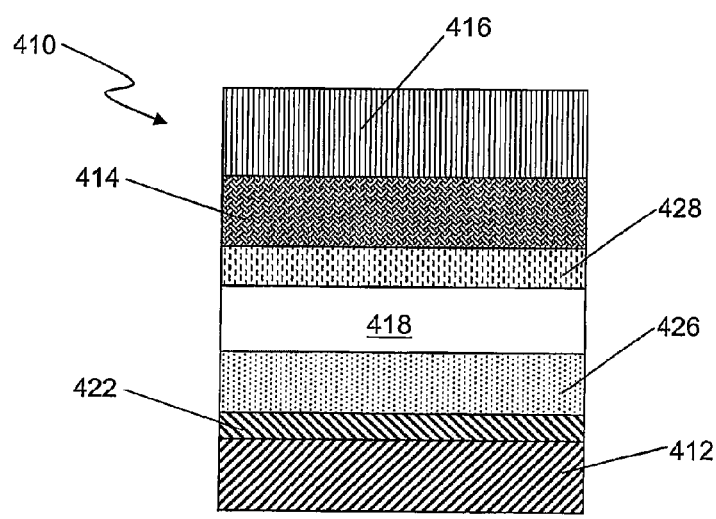
FIG. 5 is a sectional view of an exemplary composite structure according to yet a further another aspect of the invention, in which a drug layer is sandwiched between a membrane and a primer-coated containment layer.

Referring to FIG. 5, there is shown another composite structure, indicated generally at 410, according to the invention. The structure includes, in sequence, a liner film layer 412, an adhesive layer 422, an optional membrane 426, a drug layer 418, an optional primer layer 428, a containment layer 414, and a polyester film layer 416.

A detailed description of the exemplary embodiments shown in FIGS. 1-5 will now be provided.

Liner Film Layer

Liner film layer 12, 112, 212, 312, 412, also known as a release liner, is a film layer designed to be peeled off by the user before pressing the adhesive layer 22, 122, 222, 322, 422 of the composite structure to the skin to administer the drug contained in the TDD composite structure. Any of a number of release films known in the art may be used, provided that the film is suitably removable from the adhesive layer and provided that the adhesive layer can stick to the user's skin after the release film is peeled off. One suitable release film, a 76 µm thick fluoropolymer coated polyester film, is sold by 3M Corporation of St. Paul, Minn. under the name Scotchpack™ #1022. In general, non-silicone release liners with a fluoropolymer release surface are preferred, providing good release from a wide variety of skin contact adhesives including silicone, acrylate, polyisobutylene, and rubber based adhesives. However, silicone-coated or other liners may be used.

Drug Layer

Drug layer 18, 118, 218, 318, 418 may contain any of a wide variety of pharmaceutically active ingredients. These may be used for treating or preventing a variety of conditions, such as menopause-related hormone imbalances, pain, angina pectoris, and others. They may be used for smoking cessation, birth control, prevention of motion sickness, treatment of neurological disorders such as Parkinson's disease, and other conditions, and may include such exemplary ingredients as nitroglycerine, scopolamine, estradiol, and nicotine. In many cases, the drug is mixed with one or more excipients, carriers such as EVA polymers, penetration enhancers to reduce the barrier of the stratum corneum, and/or other materials. Methods and formulations for preparing compositions for drug layer 18, 118, 218, 318, 418 therefore vary broadly, and are known to the person of ordinary skill in the art relevant to the particular type of medical treatment addressed by the TDD. The term "drug layer" as used herein is intended to include drug repositories of any shape or size within a TDD. The drug layer may be a solid, semi-solid, gel, liquid, or any other form.

Adhesive Layer

Adhesive layer 22, 122, 222, 322, 422 is a contact adhesive that is capable of forming an peelable or non-permanent adhesive bond to liner film layer 12, 112, 212, 312, 412 and to the user's skin, once the liner is removed. The adhesive layer may be of any thickness, but typically will have a thickness between 10 and 100 µm. Any of a number of adhesives known in the film composite art may be used, employing known application techniques, to form adhesive layer 22, 122, 222, 322, 422. Silicone, polyacrylate, polyisobutylene, and rubber based adhesives may typically be used, usually applied from solvent solutions, and a wide variety of these is know to the person of ordinary skill in the art. One example of a suitable adhesive may be prepared by mixing a high molecular weight polyisobutene, a low molecular weight polyisobutene, and mineral oil, as described is U.S. Pat. No. 4,379,454, and applied by casting a 50 µm thick layer of the mixture onto a siliconized 75 µm thick PET release liner film.

Membrane

Membrane 26, 326, 426 may be made of a dense or microporous polymer film that has the requisite permeability to the particular drug being administered. Typical membranes include EVA films or microporous films, and are available from a variety of suppliers. Examples include CoTran™ controlled-caliper membranes, available from 3M Corporation. Although EVA membranes are exemplary, any membrane that suits the needs of the particular drug being administered is suitable for use according to the invention.

Primer Layer

Typically, when adhering a polyester film layer to other layers in the composite structure, a primer layer may be used to increase adhesion. For example, and in reference to FIGS. 1-3, primer layer 28, 128, 228 may be any of a number of materials capable of providing adequate adhesion to the layers with which it is in contact. Typical primers include polyacrylates, ethylene-acrylic acid (EAA) copolymers, amorphous polyesters, polyvinylidene chlorides (PVdC), and polyethylenimines (PEI). In particular, EAA primers generally provide good adhesion to both EVA-containing layers and polyester layers, and typically do not interact with most drugs and/or retard their rate or delivery. The primer layer, which may be provided by casting from a suitable solvent, is typically between 0.01 and 0.10 µm in thickness. EAA or other primers may also be used to improve adhesion between the containment layer and other layers. For example, and referring to FIGS. 4 and 5, the adhesion of containment layers 314, 414 to drug layers 318, 418 respectively may be enhanced by the use of primer layers 328, 428. If EAA is the primer layer, it may be applied from an aqueous solution using a gravure roller or other means known in the art. Suitable EAA copolymers may be obtained from any of a number of commercial sources, including for example PRIMACOR® resin, available from Dow Chemical of Midland, Mich., NUCREL® resins from DuPont of Wilmington, Del., and Escor® resins from ExxonMobil Chemical Co., Houston Tex.

Polyester Film Layer

Film layer 16, 116, 216, 316, 416 is a polyester film, for example a polyethylene terephthalate (PET) film or a polyethylene naphthalate (PEN) film. The film may be of any thickness less than 20 µm, but typically will have a thickness between 5 and 18 µm, more typically between 9 and 15 µm. It has been found that the use of thicknesses less than 20 µm provides greater comfort and a more flexible and aesthetically pleasing TDD than may be obtained with more commonly used PET films, which are typically between 25 and 50 µm thick.

Polyethylene terephthalate polymer preparation techniques are well known to those skilled in the art and are disclosed in many texts, such as Encyclopedia of Polymer Science and Engineering, 2nd. Ed., Vol. 12, Wiley, N.Y., pp. 1-313. The polymer is typically obtained by condensing the appropriate dicarboxylic acid or its lower alkyl diester with ethylene glycol. For example, polyethylene terephthalate is formed from terephthalic acid or an ester thereof, and polyethylene naphthalate is formed from 2,7-naphthalene dicarboxylic acid or an ester thereof.

In some embodiments of the invention, the polyester used in the film layer 16, 116, 216, 316, 416 has a glass transition temperature between 50 and 65° C., typically between 58 and 61° C., and a melting point between 228 and 240° C., typically between 232 and 238° C. The polyester may have an intrinsic viscosity within a wide range, typically between about 0.5 to about 0.8, and commonly about 0.6. For purposes of this invention, the intrinsic viscosity of a polyester is measured at 25° C. using o-chlorophenol as a solvent.

Typically, but not necessarily, the film used to form polyester film layer 16, 116, 216, 316, 416 is biaxially oriented. Biaxial orientation of the polyester film may be accomplished by stretching the composite in sequence in two mutually perpendicular directions, typically at a temperature in the range of about 78 to 125° C. The stretching operation is preferably followed by heat setting under dimensional restraint, typically at a temperature in the range 150 to 250° C. Suitable processes for stretching and heat setting are described in U.S. Pat. No. 3,107,139.

The polyester film layer 16, 116, 216, 316, 416 may also include a slip additive, which typically improves the ability of the composite structure to be handled and attached to the other layers of the composite structure without forming delaminations, fractures, pinholes, or other defects. Any slip additive may be used, such as talc, clays, etc, but typically the additive will be a silica. The total loading of slip additive will depend upon the exact type of additive, the exact composition of the polyester film layer 16, 116, 216, 316, 416, and perhaps other factors. As matte or low gloss films are preferred, the amount will be typically be between 0.5 and 3 wt % relative to the polymer making up the layer, more typically between 1 and 2 wt %. In one exemplary embodiment of the invention, 1.1% silica is used. Suitable silicas include Syloid® ED2, 244, 620, and 74 from W. R. Grace & Co., Davidson Chemical Division of Columbia, Md., and Sylysia™ silicas, available from Fuji Silysia Chemical Ltd. of Research Triangle Park, N.C. Suitable materials for making polyester film layer 16, 116, 216, 316, 416 include Melinex® 376, 377 and 378, and Mylar® EB11 polyester films, available from DuPont Teijin Films of Wilmington, Del. Such films have a 60° gloss of 50% or less, as measured by ASTM D1003. In some embodiments of the invention, polyester film layer 16, 116, 216, 316, 416 has a matte finish produced by means of mechanical abrasion such as sand matting, which tends to confer a desirable, more skin-like appearance to a TDD comprising it. Such matte films are available from a variety of sources, and have a 60° gloss of 15% or less, typically less than about 8%. Suitable examples are sold by DuPont-Teijin Films of Wilmington, Del. under the name Tetoron® sand matte films, and have a gloss of about 6%.

Containment Layer

Containment layer 14, 114, 214, 314, 414 contains between 0 and 15 wt % of vinyl acetate repeating units in the form of one or more polymers, and is typically between 3 and 15 µm in thickness. The inventors have found that, by keeping the vinyl acetate content of this layer below 15 wt %, preferably about 12 wt % or lower, reduced interactions with the drug and higher rates of drug delivery can frequently be obtained than when the layer contains a higher vinyl acetate content. Containment layer 14, 114, 214, 314, 414 is thinner than that commonly made with typical prior art materials containing only EVA polymers. Such films are typically greater than 15 µm in thickness, due to limitations in available EVA extrusion coating technology. This may make the TDD patch stiffer and less comfortable for the wearer, and more visible through the wearer's clothing. In addition, the inventors believe that greater thickness of this layer may result in less than desirable performance in some cases due to interaction of the drug with this layer, whose greater thickness may cause the layer to act as a reservoir that holds the drug and slows its release. Thus prior art EVA films prepared by solvent coating are typically too high in vinyl acetate content, while those with a lower vinyl acetate content can only be made by extrusion and are therefore too thick, for achieving the purposes of this invention. This will be discussed in more detail below.

One way to achieve the desired low level of vinyl acetate content is to use a polymer that contains no vinyl acetate repeating units at all. Thus, in some exemplary embodiments of the invention, the containment layer 14, 114, 214, 314, 414 comprises a thermal bonding copolyester resin containing no vinyl acetate, particularly a copolyester resin derived from one or more dibasic aromatic carboxylic acids, such as terephthalic acid, isophthalic acid and hexahydroterephthalic acid, and one or more glycols, such as ethylene glycol, diethylene glycol, triethylene glycol and neopentyl glycol. In addition to containing no vinyl acetate repeating units, thermal bonding copolyester resins are capable of flowing and adhering to adjacent surfaces upon application of moderate heat, thus making them convenient for assembling composite structures according to the invention.

In particular, containment layer 14, 114, 214, 314, 414 may comprise a terephthalate-containing polyester. A preferred copolyester is derived from terephthalic acid and one or both of isophthalic acid and hexahydroterephthalic acid, and one or more glycols, preferably ethylene glycol. Exemplary copolyesters that provide satisfactory bonding properties in the amorphous state are those of ethylene terephtha late and ethylene isophthalate, especially in the molar ratios 60 to 90 mol % ethylene terephthalate and correspondingly 40 to 10 mol % ethylene isophthalate. Particularly preferred copolyesters comprise 70 to 85 mol % ethylene terephthalate and 30 to 15 mol % ethylene isophthalate, for example a copolyester of approximately 80 mol % ethylene terephthalate and approximately 20 mol % ethylene isophthalate.

In manufacturing film composite structures according to the invention, it may be advantageous to provide polyester film layer 16, 116, 216, 316, 416 and containment layer 14, 114, 214, 314, 414 together in the form of a film composite. This may be formed by solvent casting or extrusion of the containment layer onto the surface of polyester film layer 16, 116, 216, 316, 416. In the case where polyester film layer 16, 116, 216, 316, 416 comprises biaxially oriented polyethylene terephthalate, and the containment layer 14, 114, 214, 314, 414 is a copolyester resin as described above, the film composite may be conveniently made by a process that includes multiple extrusion through a multiple orifice die or coextrusion of the composite layers, e.g. broadly as described in U.S. Pat. No. 3,871,947, followed by molecular orientation by stretching in one or more directions and heat setting. A convenient process and apparatus for coextrusion, known as single channel coextrusion, is described in U.S. Pat. No. 4,165,210 and GB patent specification No. 1,115,007. The method comprises simultaneously extruding streams of the first and second of two polyesters from two different extruders, uniting the two streams in a tube leading to a manifold of an extrusion die, and extruding the two polyesters together through the die under conditions of streamline flow so that the two polyesters occupy distinct regions of the flow without intermixing, thereby producing a film composite.

As noted above, biaxial orientation of the polyethylene terephthalate portions of the film composite may be accomplished by stretching the composite in sequence in two mutually perpendicular directions typically at temperatures in the range of about 70 to 110° C. Generally, the conditions applied for stretching the composite may function to partially crystallize the copolyester layer, and in such cases it is preferred to heat set the film composite under dimensional restraint at a temperature greater than the crystalline melting temperature of the copolyester layer, but lower than the crystalline melting temperature of the polyethylene terephthalate portions. The composite is then permitted or caused to cool, rendering the copolyester layer essentially amorphous while high crystallinity is maintained in the polyethylene terephthalate layer. Therefore, the stretching operation is preferably followed by heat setting under dimensional restraint, typically at a temperature in the range 170 to 200° C.

Another way to achieve the desired low level of vinyl acetate content in containment layer 14, 114, 214, 314, 414 is to combine one or more ethylene-vinyl acetate (EVA) copolymers having relatively high vinyl acetate content with other resins having no (or low) vinyl acetate content, provided that the overall vinyl acetate content of the blend is less than 15 wt %. Typically, the vinyl acetate level will be between 1 and 15 wt %, more typically between 8 and 12 wt %. The inventors have found that the use of such a blend allows the formation of a containment layer having sufficiently low vinyl acetate content that the drug release properties of the layer are very good.

Solvent coating may also allow formation of thinner coatings than are obtainable by extrusion coating, but EVA resins capable of being solvent coated alone (not in combination with another resin) typically have a vinyl acetate content of at least 28 wt % in order to enable resin solubility in the coating solvent. However, this high vinyl acetate content may result in increased interaction with the drug, retarding its release. In this regard, one advantage of the methods and composite structures provided by the invention is the ability to provide thin, low vinyl acetate films by casting from a diluent such as a solvent, thereby enabling the formation of films that are thinner than might be provided by conventional techniques such as forming a film solely from a low vinyl acetate content EVA resin by melt extrusion. Without wishing to be bound by any particular theory or explanation, it is believed that keeping the vinyl acetate content low, especially when combined with a thin containment layer, improves performance by minimizing the amount of drug that dissolves in, or otherwise associates with, the containment layer.

Exemplary compositions for forming containment layer 14, 114, 214, 314, 414 include mixtures of one or more EVA resins with one or more nonpolar polymers such as polybutenes, polyisobutylenes, ethylene/octene or ethylene/hexane copolymers, EPDM (ethylene propylene diene monomer) terpolymers, ABA block copolymers or terpolymers such as SBS (styrene-butadiene-styrene) and SEBS (styrene-ethylene/butylene-styrene) ABA block copolymers having styrenic A segments, including for example Kraton® D resins, available from Kraton® Polymers US LLC, Houston Tex. Especially suitable resins are those wherein the B segment is a saturated aliphatic segment, for example Kraton® G series resins such as Kraton® G-1650, G-1651, G-1652, G-1654X, and G-1657M. Mixtures of these types have been found to be soluble in organic solvents, and are capable of providing thin films while maintaining the low vinyl acetate content desired for making TDD's.

Typically, the ethylene-vinyl acetate component constitutes between 35 and 75 wt % of a combined weight of the ethylene-vinyl acetate component and the ABA block copolymer. Typically, in order to obtain sufficient solubility in solvents for casting the films, the EVA resin(s) will have a vinyl acetate content of at least 23 wt %. A single EVA can be used, particularly if the EVA comprises acrylic or methacrylic acid repeating units, which are believed to promote good adhesion to a variety of substrates. Such a resin may, however, be used as one of the EVA's in a mixture of two or three EVA resins, as described below. Suitable levels of acrylic or methacrylic acid repeating units may be any level, but typically will be between 0.1 and 10 wt % of the resin. One suitable choice is Elvax® 4260 EVA, which contains 28 wt % vinyl acetate and 1 wt % methacrylic acid repeating units and is sold by DuPont of Wilmington, Del.

Use of a mixture of two or more EVA polymers may improve adhesion to a wide range of substrates such as membranes, and enable good bond strength across a range of bonding temperatures due to the different EVA melt points. This may provide better performance and flexibility in bonding to a variety of substrates. Thus, in some embodiments, the ethylene-vinyl acetate component comprises a first EVA polymer containing between 26 and 30 wt % of vinyl acetate repeating units and a second EVA polymer containing between 31 and 35 wt % of vinyl acetate repeating units. The EVA component may further comprise a third EVA polymer containing between 36 and 42 wt % of vinyl acetate repeating units. The first and second EVA polymers each contribute between 25 and 95 wt % of the total EVA component, and the third EVA polymer (if present) contributes between 5 and 25 wt %.

Suitable EVA resins may be obtained commercially from any of a number of manufacturers. Examples include Elvax® 265, 3180, 3182, 3190 and 4260 UE653-04 available from Ichemco, Cuggiono (MI) Italy, Escorene® UL7720 (all with 28 wt % vinyl acetate); Elvax® 3185 and Escorene® Ultra UL7840 (all with 33% vinyl acetate); and Elvax® 40W, 40L-03, and 40L-08 (all with 40 wt % vinyl acetate). Escorene® resins are available from ExxonMobil Chemical Co. of Houston Tex.

Compositions for making containment layer 14, 114, 214, 314, 414, if based on one or more EVA resins and nonpolar polymers, typically also contain a tackifier resin. Many such resins are available, and the choice will depend on the particular combination of EVA and nonpolar polymer used, as well as perhaps other factors. One suitable class of tackifiers includes polyterpene resins such as Sylvares™ 7115, available from Arizona Chemical, Jacksonville, Fla. Other useful additives may be included as well, and their application will be known to those of ordinary skill in the art. Such other additives may include, as nonlimiting examples, slip additives and anti-block silica gels. Exemplary slip additives include synthetic waxes such as Kemamide® E and Kemamide® W20, sold by Witco Corp. of Dublin, Ohio, while exemplary silica gels include Syloid® 244 and Syloid® 620, available from Davison Chemical Division of W.R. Grace & Co., Columbia, Md.

Containment layer 14, 114, 214, 314, 414 may be formed by applying to an appropriate layer, depending upon the particular embodiment of the invention being prepared, a liquid mixture comprising a diluent, the EVA component, and one or more nonpolar polymers, followed by removal of the diluent. The diluent is typically an organic liquid, and may be a solvent for one or both of the EVA and the nonpolar polymer. Thus, the mixture may comprise a dispersion or one or more of the polymers in which the dispersed polymer is insoluble or swelled, a solution of one or more of the polymers, or a combination of these. Application of the liquid mixture may be performed by any method known in the art, including for example gravure roller coating. Removal of the diluent may be by any convenient means, including for example heating, blowing with air, or removing under vacuum. The resulting film may be of any thickness, but is usually less than 20 μm in thickness, typically between 5 and 15 μm in thickness, more typically between 11 and 14 μm. For example, a thickness of about 12.5 μm may be used. The film may comprise a homogeneous mixture of the polymers, an interpenetrating network of two or more of the polymers, or a dispersion of one or more of the polymers in one or more of the other polymers. After forming the coating, drug layer 18, 118, 218, 318, 418, or primer layer 16, 116, 216, 316, 416, or adhesive layer 22, 122, 222, 322, 422 may be formed upon it. If it is a primer layer or an adhesive layer, a drug layer is subsequently formed on the surface of that layer.

As shown in FIGS. 1, 4, and 3, the containment layer 14, 314 or the adhesive layer 222 respectively may comprise a concave depression 20, 320, or 220 partially enclosing the drug layer 18, 318, 218. Such a depression may typically be formed by heating an assembly of layers including the containment or adhesive layer to soften the material, and pressing the softened layer against the corresponding drug layer 18, 318, 218 mounted on membrane 26, 326 or liner film layer 212, respectively. It will be appreciated that a considerable variety of processing methods and assembly sequences may be used to make composite structures according to FIGS. 1-5, and all of these are to be considered within the scope of this invention.

Example

A layer comprising an EVA component and a styrenic ABA block copolymer is prepared from the following ingredients in the wt % amounts indicated.

| | |
|---|---|
| Styrene-ethylene/butylene-styrene ABA block copolymer | 33% |
| Polyterpene tackifier resin | 25% |
| EVA with 33% vinyl acetate content | 18% |
| EVA with 28% vinyl acetate content, 1% methacrylic acid content | 16% |
| EVA with 33% vinyl acetate content | 5.4% |
| Synthetic waxes | 1.2% |
| Anti-block silica gels | 1.5% |

The above ingredients are dissolved in an 80/20 wt/wt toluene/tetrahydrofuran mixture at a 15-20% solids level and applied to a 12 μm thick PET film (Melinex® 377) bearing an EAA primer coating, on the side bearing the primer, using a gravure roller, followed by evaporation of the solvent by blowing with warm air at 80-90° C. The resultant film has an approximately 12 wt % vinyl acetate repeating unit content and thickness of about 9-10 μm. Thus the final thickness of the combined PET and coating composition is about 22 μm, much thinner than typical prior art structures which are about 33-50 μm thick.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A method of making a composite structure, the method comprising in sequence:
(a) applying to a surface of a substrate a liquid mixture comprising a diluent, an ethylene-vinyl acetate component, and a nonpolar polymer; and
(b) removing the diluent to provide a coating containing between 1 and 15 wt % of vinyl acetate repeating units, provided that the coating does not include any drug;
wherein the nonpolar polymer comprises an ABA block copolymer wherein the A segments of the block copolymer are styrenic segments and wherein the B segments of the block copolymer are saturated aliphatic segments;
wherein the substrate comprises a polyester film layer and wherein the surface of the substrate is a surface of the polyester film layer or a surface of a primer layer residing on a surface of the polyester film layer, wherein the primer layer comprises a polymer selected from the group consisting of polyacrylates, ethylene-acrylic acid copolymers, amorphous polyesters, polyethylenimines, and polyvinylidene chlorides;
and wherein the substrate is not a removable release liner.

2. The method of claim 1, wherein the ethylene-vinyl acetate component constitutes between 35 and 75 wt % of a combined weight of the ethylene-vinyl acetate component and the ABA block copolymer.

3. The method of claim 1, wherein the polyester film layer is less than 20 μm in thickness, the method further comprising (c) applying to the coating a drug layer.

4. The method of claim 1, wherein the polyester film layer is less than 20 μm in thickness, the method further comprising:
(c) applying a primer layer to the coating.

5. The method of claim 4, further comprising:
(d) applying a drug layer to the primer layer applied in step (c).

6. The method of claim 4, wherein the primer layer applied in step (c) comprises a polymer selected from the group consisting of polyacrylates, ethylene-acrylic acid copolymers, amorphous polyesters, polyethylenimines, and polyvinylidene chlorides.

7. The method of claim 4, wherein the primer layer applied in step (c) comprises an ethylene-acrylic acid copolymer.

8. The method of claim 1, wherein the polyester film layer is less than 20 μm in thickness, the method further comprising:
(c) applying an adhesive layer to the coating.

9. The method of claim 8, further comprising:
(d) applying a drug layer to the adhesive layer.

10. The method of claim 1, wherein the liquid mixture further comprises a tackifier.

11. The method of claim 10, wherein the tackifier is a polyterpene resin.

12. The method of claim 1, wherein the ethylene-vinyl acetate component comprises acrylic acid units.

13. The method of claim 1, wherein the ethylene-vinyl acetate component comprises methacrylic acid units.

14. The method of claim 4, wherein coating has a thickness in a range from 3 μm to 15 μm.

15. The method of claim 1, wherein the surface of the substrate is said surface of the polyester film layer.

16. The method of claim 1, wherein the primer layer comprises an ethylene-acrylic acid copolymer.

* * * * *

UNITED STATES PATENT AND TRADEMARK OFFICE
CERTIFICATE OF CORRECTION

| | |
|---|---|
| PATENT NO. | : 8,840,920 B2 |
| APPLICATION NO. | : 12/890291 |
| DATED | : September 23, 2014 |
| INVENTOR(S) | : Peter N. Nugara et al. |

It is certified that error appears in the above-identified patent and that said Letters Patent is hereby corrected as shown below:

In the Claims

At Column 11, line 7, "The method of claim 4," should read --The method of claim 1,--.

Signed and Sealed this
Twenty-third Day of December, 2014

Michelle K. Lee
*Deputy Director of the United States Patent and Trademark Office*